United States Patent [19]

Eckenhoff et al.

[11] Patent Number: 5,223,266
[45] Date of Patent: Jun. 29, 1993

[54] LONG-TERM DELIVERY DEVICE WITH EARLY STARTUP

[75] Inventors: James B. Eckenhoff, Los Altos; Terry L. Burkoth, Palo Alto; John P. Carr, Sunnyvale; Jeremy C. Wright, Los Altos, all of Calif.

[73] Assignee: Alza Corporation, Palo Alto, Calif.

[21] Appl. No.: 876,734

[22] Filed: Apr. 27, 1992

Related U.S. Application Data

[60] Continuation-in-part of Ser. No. 850,087, Mar. 12, 1992, which is a division of Ser. No. 469,861, Jan. 24, 1990, abandoned.

[51] Int. Cl.⁵ .............................................. A61K 9/24
[52] U.S. Cl. ................................ 424/473; 424/438; 424/468
[58] Field of Search .................................... 424/473

[56] References Cited

U.S. PATENT DOCUMENTS

| | | | |
|---|---|---|---|
| 4,077,407 | 3/1978 | Theeuwes et al. | 128/260 |
| 4,160,020 | 7/1979 | Ayer et al. | 424/15 |
| 4,200,098 | 4/1980 | Ayer et al. | 128/260 |
| 4,327,725 | 5/1982 | Cortese et al. | 128/260 |
| 4,381,780 | 5/1983 | Holloway | 604/892 |
| 4,578,263 | 3/1986 | Whitehead | 424/15 |
| 4,595,583 | 6/1986 | Eckenhoff et al. | 424/15 |
| 4,612,186 | 9/1986 | Eckenhoff et al. | 424/15 |
| 4,624,945 | 11/1986 | Eckenhoff et al. | 514/30 |
| 4,643,731 | 2/1987 | Eckenhoff | 604/892 |
| 4,663,148 | 5/1987 | Eckenhoff et al. | 424/454 |
| 4,663,149 | 5/1987 | Eckenhoff et al. | 424/452 |
| 4,675,174 | 6/1987 | Eckenhoff | 424/ |
| 4,678,467 | 7/1987 | Eckenhoff et al. | 604/892 |
| 4,684,524 | 8/1987 | Eckenhoff et al. | 424/469 |
| 4,692,336 | 9/1987 | Eckenhoff et al. | 424/468 |
| 4,704,118 | 11/1987 | Eckenhoff | 604/892 |
| 4,716,031 | 12/1987 | Eckenhoff et al. | 424/453 |
| 4,717,566 | 1/1988 | Eckenhoff et al. | 424/438 |
| 4,717,568 | 1/1988 | Eckenhoff et al. | 424/469 |
| 4,717,718 | 1/1988 | Eckenhoff et al. | 514/30 |
| 4,729,793 | 3/1988 | Eckenhoff et al. | 106/169 |
| 4,772,474 | 9/1988 | Eckenhoff et al. | 424/465 |
| 4,781,714 | 11/1988 | Eckenhoff et al. | 604/890.1 |
| 4,800,056 | 1/1989 | Eckenhoff et al. | 264/129 |
| 4,814,180 | 3/1989 | Eckenhoff et al. | 424/473 |
| 4,844,984 | 7/1989 | Eckenhoff et al. | 424/438 |
| 4,872,873 | 10/1989 | Zingerman | 604/892.1 |
| 4,927,419 | 5/1990 | Scully | 604/892.1 |
| 5,045,082 | 9/1991 | Ayer et al. | 604/892.1 |

FOREIGN PATENT DOCUMENTS

WO8600519 1/1986 World Int. Prop. O. .

*Primary Examiner*—Thurman K. Page
*Assistant Examiner*—D. Gabrielle Phelan
*Attorney, Agent, or Firm*—Jacqueline S. Larson; Paul L. Sabatine; Steven F. Stone

[57] ABSTRACT

The present invention is directed to an improvement in a delivery device, the device comprising a wall that surrounds an internal lumen or compartment which contains a beneficial agent or medicament formulation, an expandable driving member and an optional density member, and having an a exit means, and wherein the improvement comprises prehydrating the delivery device as a means for advancing the beginning or startup of agent delivery from the delivery system to give earlier release of beneficial agent to the environment of use. An embodiment of the invention concerns a fluid reservoir in contact with the expandable driving member to provide prehydration of the device.

31 Claims, 3 Drawing Sheets

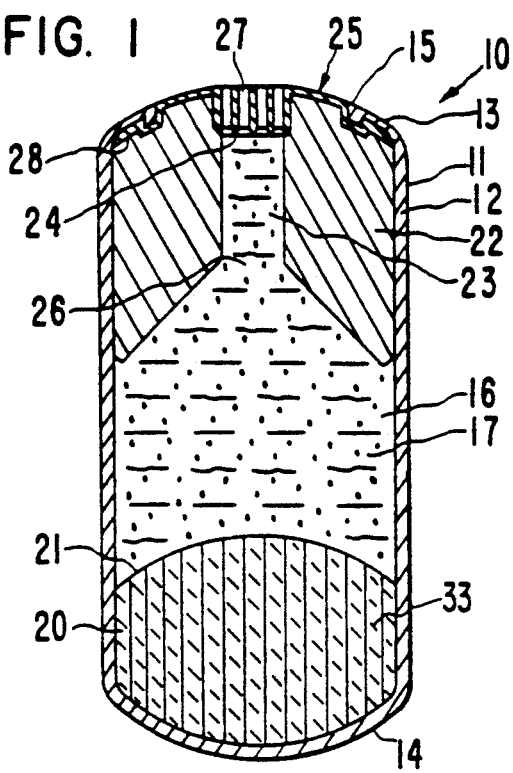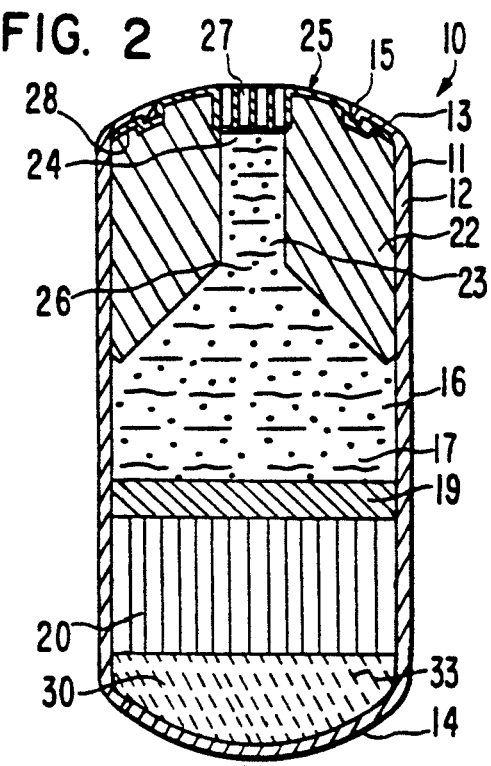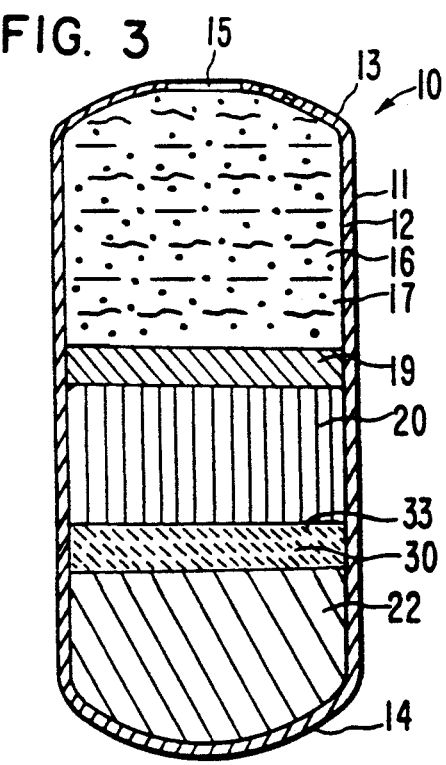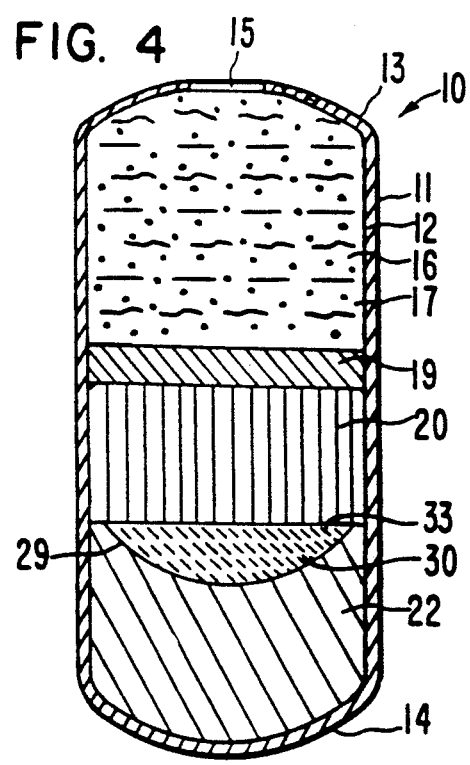

LONG-TERM DELIVERY DEVICE WITH EARLY STARTUP

REFERENCE TO RELATED APPLICATION

This application is a continuation-in-part of application Ser. No. 07/850,087, filed Mar. 12, 1992, pending which is a division of application Ser. No. 07/469,861, filed on Jan. 24, 1990, abandoned.

FIELD OF THE INVENTION

This invention relates to an improvement in long-term osmotically-actuated delivery devices, wherein the improvement comprises means for advancing the beginning of agent delivery from the device.

BACKGROUND OF THE INVENTION

Agent delivery systems and devices which use an expansion means can deliver a beneficial agent to an environment of use over a period of hours, days, or months. The expansion means absorbs liquid, expands, and acts to drive out beneficial agent formulation from the interior of the device in a controlled manner. Such delivery systems are well known to the prior art and include, for example, U.S. Pat. Nos. 4,077,407; 4,160,020; 4,200,098; 4,327,725; 4,595,583; 4,612,186; 4,624,945; 4,643,731; 4,663,148; 4,663,149; 4,675,174; 4,678,467; 4,684,524; 4,692,336; 4,704,118; 4,716,031; 4,717,566; 4,717,568; 4,717,718; 4,729,793; 4,772,474; 4,781,714; 4,800,056; 4,814,180; and 4,844,984.

Agent delivery devices utilizing an expansion means can be designed to deliver agent over an extended or prolonged period of time, i.e., 25-30 days or greater, and especially 60-120 days or greater. Such devices generally comprise a slowly permeable semipermeable membrane, together with a beneficial agent in a carrier which is viscous or paste-like and is extruded by the action of the expansion means over an extended time. Devices having an osmotic expandable member require a "startup" period of time for the expandable member to become activated and begin to push against the beneficial agent formulation to deliver beneficial agent to the environment of use at the desired constant rate. The startup time of the device depends upon the rate at which the semipermeable membrane allows hydration of the system and the rate at which the expansion means becomes hydrated sufficiently to begin extrusion of the beneficial formulation.

Prior art devices which have been designed to maintain continuous dosages of a beneficial agent for extended periods of time, while being extraordinarily effective for delivering beneficial agents that are hydrophilic, hydrophobic, lipophilic or lipophobic to a biological environment of use, have the disadvantage of exhibiting a significant startup time, usually of at least several days and often of up to several weeks, between administration to the subject animal or human and the onset of agent delivery at the desired rate. Therefore, it is desirable to provide means for shortening the time needed for the delivery system to start delivering a beneficial agent.

SUMMARY OF THE INVENTION

Accordingly, it is a principle object of this invention to provide a novel and useful delivery system or device that overcomes the disadvantages associated with the prior art.

It is another object of the present invention to provide a long-term dispensing device that quickly and continuously delivers an effective amount of agent, followed by a continuous and sustained delivery of agent over a prolonged period of time.

A further object of the invention is to provide a delivery device that is prehydrated with a pharmaceutically acceptable fluid to provide an early startup of delivery of beneficial agent from the delivery device.

Yet another object of the invention is to provide substantially immediate delivery of beneficial agent to the animal upon delivery of a delivery device to the animal by prehydrating the delivery device to overcome the time required for fluid to be imbibed into the delivery device.

A still further object of the invention is to provide a beneficial agent delivery device for dispensing a beneficial agent to an animal, which delivery device comprises an osmotically activated expansion means and which further comprises a fluid reservoir in contact with the expansion means, which reservoir hydrates the expansion means.

These and other objects are met by the present invention which relates to an improvement in a delivery device, the device comprising a wall that surrounds an internal lumen or compartment which contains a beneficial agent or medicament formulation, an expandable driving member and an optional density member, and having an exit means, and wherein the improvement comprises prehydrating the delivery device as a means for advancing the beginning or startup of agent delivery from the delivery system to give earlier release of beneficial agent to the environment of use. An embodiment of the invention concerns a fluid reservoir in contact with the expandable driving member to provide prehydration of the device.

Other objects, features and advantages of the invention will be more apparent to those skilled in the dispensing art from the following detailed description of the specification, taken in conjunction with the drawings and the accompanying claims.

BRIEF DESCRIPTION OF THE DRAWINGS

FIG. 1 shows in cross-sectional view one embodiment of the delivery device of the present invention.

FIG. 2 shows in cross-sectional view another embodiment of the delivery device of the present invention.

FIG. 3 shows in cross-sectional view yet another embodiment of the delivery device of the present invention.

FIG. 4 shows in cross-sectional view a further embodiment of the delivery device of the present invention.

DETAILED DESCRIPTION OF THE INVENTION

Figure 5:
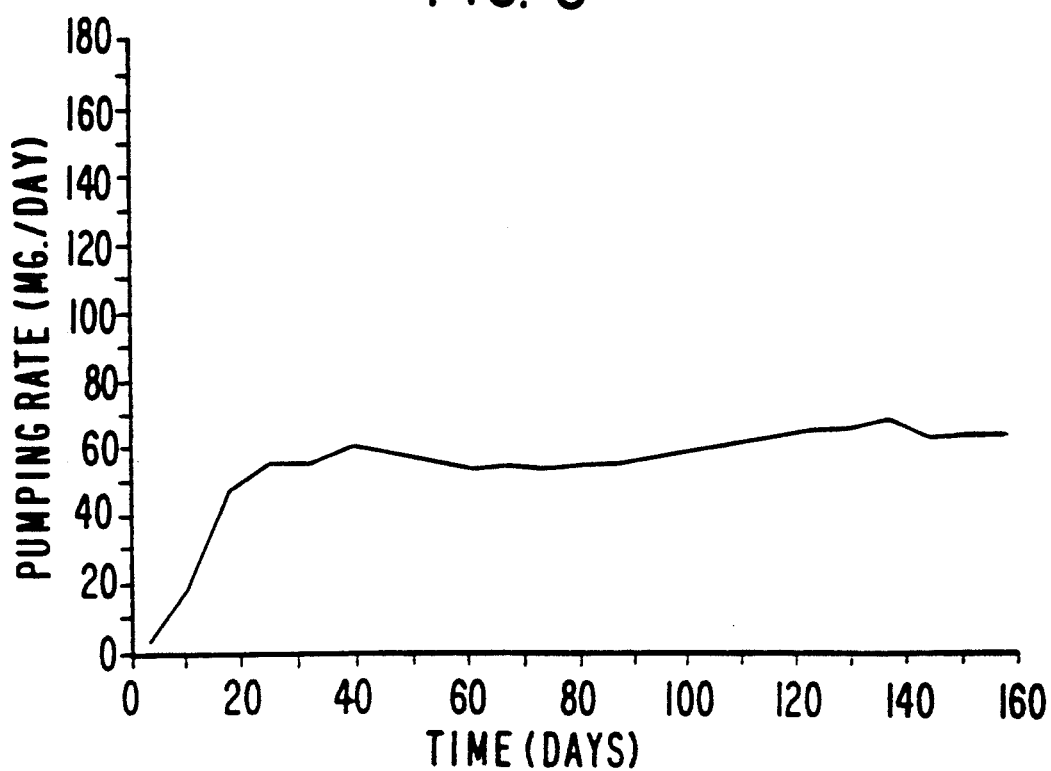
FIG. 5 is a graph that depicts the release rate pattern of a prior art delivery device that has not been prehydrated.

The present invention provides new and useful therapeutic delivery systems for dispensing a beneficial agent to an environment of use with little or no delay to startup of delivery of the agent. These devices are prehydrated with a pharmaceutically acceptable fluid to give an early startup.

FIG. 1 depicts in cross-section a prehydrated delivery device 10 provided by the invention. Device 10 is manufactured as a dispenser comprising a body 11 formed by a wall 12 and having a lead end 13, a trailing or rear end 14, and opening 15 in the lead end. Wall 12 surrounds an internal lumen or compartment 16. Wall 12 comprises, in a presently preferred embodiment, a semipermeable wall-forming composition that is substantially permeable to the passage of an external fluid into compartment 16 and is substantially impermeable to the passage of a beneficial agent and other ingredients contained in delivery device 10. In another embodiment, wall 12 comprises at least in part a semipermeable composition with the remainder of the wall comprising a different composition substantially impermeable to the passage of fluid as well as of the ingredients in the device. Materials useful as wall-forming compositions are well known in the art, examples of which are described in the patents previously cited herein, the disclosures of which are incorporated herein by reference. Wall 12 is non-toxic and it maintains its physical and chemical integrity, that is, it does not erode during the dispensing period. Device 10, in a presently preferred embodiment, is manufactured with wall 12 as a single unit member, by injection molding or the like.

Compartment 16 contains a beneficial agent formulation 17, which comprises a beneficial agent together with a carrier for the beneficial agent. The carrier material may be a fluid, solid, a semi-solid or, in a presently preferred embodiment, a thermo-responsive composition. Materials suitable as carriers for the beneficial agent are known in the art and are described in the patents previously cited herein.

Compartment 16 further contains displacement means or expandable driving member 20 that is in layered contact with a contacting surface 21 of beneficial agent formulation 17. The expandable driving member usually comprises a fluid-imbibing and fluid-retaining composition such as an osmotically effective solute (also known as an osmagent) or a hydrogel composition, which includes a swellable, expandable polymer (also known as an osmopolymer), as well as mixtures of an osmagent with an osmopolymer. The expandable driving member, by absorbing fluid from a fluid environment of use through semipermeable wall 12, provides a driving source for delivering the beneficial agent formulation from compartment 16 to the environment of use via an exit means. Materials which are appropriate for use in forming the expandable fluid-activated driving member are known to the art, examples of which are described in the patents previously cited herein.

Both formulation 17 and expandable member 20 have a shape that corresponds to the internal shape of wall 12 and compartment 16. Compartment 16 also contains a density member or densifier 22 that is in contact with beneficial agent formulation 17, which density member 22 is positioned in compartment 16 distant from expandable member 20 and adjacent opening 15. Density member 22 comprises a passageway or bore 23 with an opening 24 adapted for receiving in tight relationship an exit member 25 having exit passageways 27 surrounded by a supporting shoulder 28. Shoulder 28 receives wall 12 in a curved shoulder relation to keep exit member 25 firmly inside compartment 16. Density member 22 also comprises an opening 26 for letting beneficial agent formulation 17 flow from compartment 16 to exit member 25 and hence to the exterior of delivery device 10 and into the environment of use. Density member 22 is designed for keeping device 10 in the rumen of an animal over a prolonged period of time.

A prehydration permeant 33 is present in expandable member 20 for providing prehydration of expandable member 20 and thus for providing an early startup of delivery of beneficial agent formulation 17 into the environment.

Delivery device 10 can be prehydrated with a prehydration permeant 33 by immersion, partial immersion, dipping, spraying, or the like in or with a permeant 33 such as water, distilled water, purified water (USP), a buffer, a physiologically or pharmaceutically acceptable fluid such as saline, mixtures thereof, composites thereof with other additives such as a biostat, and the like. The device can alternatively be prehydrated by placing a prehydration permeant together with the delivery device into a closed impermeable package. The basic requirements of the prehydration permeant are that the permeant is inert in the delivery device, is compatible with the other ingredients and components of the device and any packaging, and is non-toxic to an animal or human.

Alternatively, a delivery device according to the present invention may include a prehydration permeant placed into the device at the time of manufacture. The prehydration permeant is normally positioned so that it is in contact with the expandable driving member. One embodiment of such a device is illustrated in FIG. 2, which shows a delivery device 10 which comprises a body 11, a wall 12, lead end 13, rear end 14, opening 15, exit member 25 having exit passageways 27 surrounded by a supporting shoulder 28, internal compartment 16, beneficial agent formulation 17, expandable driving member 20 and density member 22 having a bore 23 and openings 24 and 26. In FIG. 2, beneficial agent formulation 17 is separated from expandable member 20 by a partition lamina or layer 19. Partition layer 19 is positioned between agent formulation 17 and expandable member 20 for substantially reducing diffusion, migration, entrapment, or the like of beneficial agent into expandable member 20. Partition layer 19 also protects the active agent formulation from any possible interaction with the expandable member 20 or the prehydration permeant 33, thereby improving the stability of the active agent formulation. In one presently preferred embodiment, layer 19 is made from a soft or a flexible polymeric composition for aiding in pushing the maximum amount of beneficial agent formulation 17 from delivery device 10. Layer 19 in operation functions like a piston, and it is so constructed to movably provide and maintain a tight piston-head arrangement between the active agent phase and the expandable phase in compartment 16.

In FIG. 2, there is present in compartment 16 a permeant reservoir 30 containing a prehydration permeant 33. Reservoir 30 is in contacting arrangement with expandable member 20 for providing prehydration to the expandable member. In this way, the permeant fluid 33 will migrate from reservoir 30 and distribute into expandable member 20 to prehydrate the expandable member prior to administration of device 10 into the environment of use. Reservoir 30 may be an empty space in compartment 16 into which is placed the prehydration permeant during manufacture of device 10 or it may be a porous material into which the prehydration permeant has been absorbed prior to or at the time of placement in device 10.

The porous material is preferably rigid and is shaped to conform to the internal configuration of wall 12 and compartment 16. The rigid reservoir can allow permeant loss from all surfaces or restricted to permeant loss from only a particular surface in contact with the expandable driving member. The porous material is selected to maintain its original shape and not change dimensions upon loss of permeant. Thus, the permeant reservoir can be made of any porous material that imbibes a fluid without significant dimensional change and which does not have significant attraction for the permeant fluid, such as hydrogen bonding or the like. The porous material should be compatible with the permeant fluid and with the other ingredients within delivery device 10. Suitable materials may be chosen from a wide variety including polymers and ceramics, two examples being porous polyethylene (Porex ®) and Accurel ®.

FIG. 3 illustrates another embodiment of the invention comprising a permeant reservoir. Device 10 in FIG. 3 comprises a body 11, a wall 12, lead end 13, rear end 14, opening 15 which functions in this embodiment as the exit means, internal compartment 16, beneficial agent formulation 17, partition layer 19, expandable driving member 20 and density member 22. In FIG. 3, density member 22 is positioned at rear end 14 opposite exit opening 15, and the permeant reservoir 30 containing prehydration permeant 33 is positioned between the density member 22 and driving member 20 and is in contact with the driving member.

FIG. 4 illustrates another embodiment of the delivery device of the invention. Device 10 in FIG. 4 is similar to the device of FIG. 3 except that permeant reservoir 30 containing prehydration permeant 33 is within the space formed by concave surface 29 of density member 22 adjacent expandable driving member 20.

While FIGS. 1 through 4 illustrate various delivery devices 10 that can be made according to the invention, it is to be understood that these delivery devices are not to be construed as limiting the invention, as the delivery device designed as a dispenser can take other shapes, sizes and forms for delivering beneficial agents to a biological environment of use. While the FIGS. all illustrate the presence of a density element, such density element is not critical to the invention, and devices according to the present invention without a density element are contemplated. Such devices are particularly suitable as implants for use with humans or animals.

The delivery device can be prehydrated with a permeant for 1 hour to 18 days or longer and at any temperature, usually at from about 20° C. to about 50° C. The prehydration is provided to reduce agent delivery startup time or to provide early agent delivery, especially when delivered to a human or an animal. Dependent on the manufacture, a prior art delivery device that has not been prehydrated can exhibit a 2- to 3-week startup period prior to onset of delivery of the agent, while a prehydrated delivery device according to the present invention begins to deliver agent during the first week after placement in the environment of use. Thus, the present invention shortens the time to startup of delivery of agent, providing an early startup. In a preferred embodiment, agent delivery is substantially immediate; that is, onset of delivery begins within 24 hours after placement in the environment of use.

The volume of prehydration permeant introduced into a delivery device is usually from about 0.025 g to 10 g of permeant, and preferably from about 0.1 g to about 3 g of permeant. The amount of permeant imbibed into a delivery device usually is greater than 1% by weight of the displacement means or expandable driving member, and in a presently preferred amount is of from about 5% to 40% of the weight of the expandable driving member. The amount of prehydration permeant imbibed should not be so great that it allows the expandable driving member to expand to such an extent that the driving member begins to deliver beneficial agent out of the delivery device prior to the time the device is administered to the environment of use. The preferred amount of prehydration permeant will be that amount which provides substantially complete hydration of the driving member but no significant expansion of the driving member prior to placement in the environment of use beyond taking up any slack in the device, caused by such things as dimensional clearances, flexibility, and the like.

The presently preferred environment of use is the rumen of an animal. However, the devices are not restricted to use in ruminant animals or to a rumen as an environment of use. Long-term dispensing devices of the invention find use, for example, in humans or other animals. The environment of use can comprise a body cavity such as the peritoneum, vagina, or intestinal tract. The devices may also be utilized as a subcutaneous implant. A single dispensing device or several dispensing devices can be administered to a subject during a therapeutic program.

The "prolonged" delivery of agent refers to delivery of beneficial agent which continues for a period of 23 days or longer, generally 60 days or longer, and preferably for 120 days or longer.

The term "beneficial agent" as used herein describes any beneficial agent or compound that can be delivered by a device herein to produce a beneficial and useful result. The term "beneficial agent" includes medicines or drugs, such as inorganic or organic drugs, nutrients, vitamins, food supplements and other agents that benefit an animal, including a warm-blooded animal, and humans. The amount of agent present in a delivery system 10 can be from 10 ng to 40 g or more. The delivery system can house various amounts of the beneficial agent, for example, 75 ng, 1 mg, 5 mg, 100 mg, 250 mg, 750 mg, 1.5 mg, 2 g, 5 g, 10 g, 15 g, and the like.

Representative of beneficial agents that can be dispensed using the delivery system of this invention include anthelmintics such as mebendazole, levamisole, albendazole, cambendazole, fenbendazole, parbendazole, oxfendazole, oxybendazole, thiabendazole, trichlorfon, praziquantel, morantel and pirantel, and the like; antiparasitic agents such as avermectins and ivermectin, ronnel, coumaphos, dichlorvos, and the like; antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; monensin and monensin sodium; Elfazepa®; dexamethasone; flumethasone; rumen fermentation manipulators and ionophores such as lysocellin, tetronasin, laidlomycin, laidlomycin butryate, laidlomycin propionate, lasalocid, virginiamycin, and the like; minerals and mineral salts; anti-bloat agents such as organopolysiloxanes and poloxalene; hormone growth supplements such as stilbestrol; estrus suppression agents such as melengestrol acetate; vitamins; antienteritis agents such as furazolidone; nutritional supplements such as methionine, lysine monohydrochloride, magnesium carbonate, sodium selenite, cobalt, and the like; various proteins and peptides; feed-through larvicides such as rabon, methoprene, and diflubenzuron; and the like.

The terms "exit means" and "exit passageway", as used herein, comprise means and methods suitable for the metered release of a beneficial agent formulation 17 from compartment 16 of the delivery device of the present invention. The exit means includes at least one passageway, orifice, or the like for communicating the internal compartment with the environment of use.

The following examples are merely illustrative of the present invention and they should not be construed as limiting the scope of the invention in any way, as these examples and other equivalents thereof will become more apparent to those skilled in the dispensing art in light of the present disclosure, the drawings and the accompanying claims.

EXAMPLE 1

A non-prehydrated delivery system manufactured in the shape of a dispenser adapted for the controlled delivery of ivermectin to an animal was made as follows.

First, a membrane cup in the shape of a dispenser was injection molded from a wall-forming composition comprising 50.0% cellulose acetate butyrate 171-15 having a 17.1% butyryl content, a 29.5% acetyl content and a 1.5% hydroxyl content; 17.3% cellulose acetate 398-10 having a 39.8% acetyl content; 21.8% Citroflex® 4 tributyl citrate; 5.9% Citroflex® 2 triethyl citrate; 4.0% polyethylene glycol 400; and 1.0% titanium dioxide. The final injection molded cup weighed about 10 grams.

Next, an expandable driving member designed as an osmotic tablet was manufactured in a shape that corresponds to the internal shape of the injection molded cup. The expandable driving member composition comprised 2.5 g of sodium chloride, 5.8 g of the sodium salt of polyacrylic acid polymer available as Carbopol® 934P, 0.07 g of Povidone® polyvinyl pyrrolidone, and 0.10 g of magnesium stearate. The composition was compressed under 10 tons into an osmotic expansion tablet, 0.850 inches in diameter, 0.66 inches in height, and having a tablet density of approximately 1.56 g/cc.

Next, 600 g of ivermectin was added with high shear mixing at 90° C. to 3320 g of microcrystalline food grade wax, having a melting point of 150°-160° F. and a Saybolt viscosity at 210° F. of 75/90, and 80 g of silicon dioxide. The silicon dioxide increases the viscosity and yield stress of the ivermectin-containing formulation. The three ingredients were blended with a rotor stator blade at 90° C. for 30 minutes. Then, the high shear a mixing was turned off and the anchor and impeller blades were activated at 35% speed, followed by pulling 10 inches of Hg vacuum for 30 minutes. Then, the mixture was cooled to approximately 74° C., the impeller blade was turned off and the vacuum was released. Next, the mixing tank was pressurized to 5 psi using nitrogen gas to give the ivermectin beneficial agent formulation.

Next, 490 g of food grade microcrystalline wax, as described in the paragraph immediately above, was added to 490 g of a food grade microcrystalline wax having a 180°-190° F. melting point and a Saybolt viscosity at 210° F. of 75/90, and the mixture was heated to 90° C. Then, 20 g of silicon dioxide was added to the molten waxes and the mixture blended using a high shear rotor stator blade for 10 minutes. After 10 minutes of mixing, the high shear rotor stator blade was turned off and 10 inches of Hg pulled on the resulting mixture for 30 minutes to give the partition layer formulation.

The dispenser was assembled by first placing the osmotic expansion tablet into the membrane cup. The membrane cup was preheated at 60° C. for about 5 minutes. Next, 1.95 g of the partition layer formulation was added to the membrane cup in contacting relation with the osmotic expansion tablet. After cooling for 2 to 6 minutes, 9.5 g of the formulation comprising the ivermectin was added to the membrane cup, followed by cooling the cup to 60° C. for 8 minutes. Then, a density element comprising iron with a central bore and dimensioned to conform to the inside of the membrane cup was placed into the cup. The density element was preheated to 65° C. and inserted into the membrane cup until the bottom of the density element contacted the thermo-responsive ivermectin formulation. An exit member made from nylon polymer as a grid, such as illustrated in FIGS. 1 and 2, with a plurality of openings of approximately 18 mesh was placed in the exit bore of the density element.

Next, the membrane cup was rotated in front of a hot air gun until the tip of the membrane softened and became thermoplastic. The membrane cup next was placed into a crimping fixture pressurized with 90 psi compressed air, followed by a crimping head activated, positioned and rotated on top of the membrane cup for 15 seconds to close over the edges of the exit member to yield the dispenser.

Accompanying FIG. 5 depicts the release rate profile for ivermectin from a dispenser made according to this example.

EXAMPLE 2

A prehydrated delivery device according to the present invention for the controlled delivery of the beneficial drug ivermectin with instant start-up was made following the procedures of Example 1, except as follows: After assembly, the delivery device of Example 1 was prehydrated for 18 days at 40° C. in deionized water, after which the prehydration temperature was ramped down over 8 days at approximately 2°-3° C. per day. The delivery system was packaged and stored for at least one week prior to use.

Figure 6:
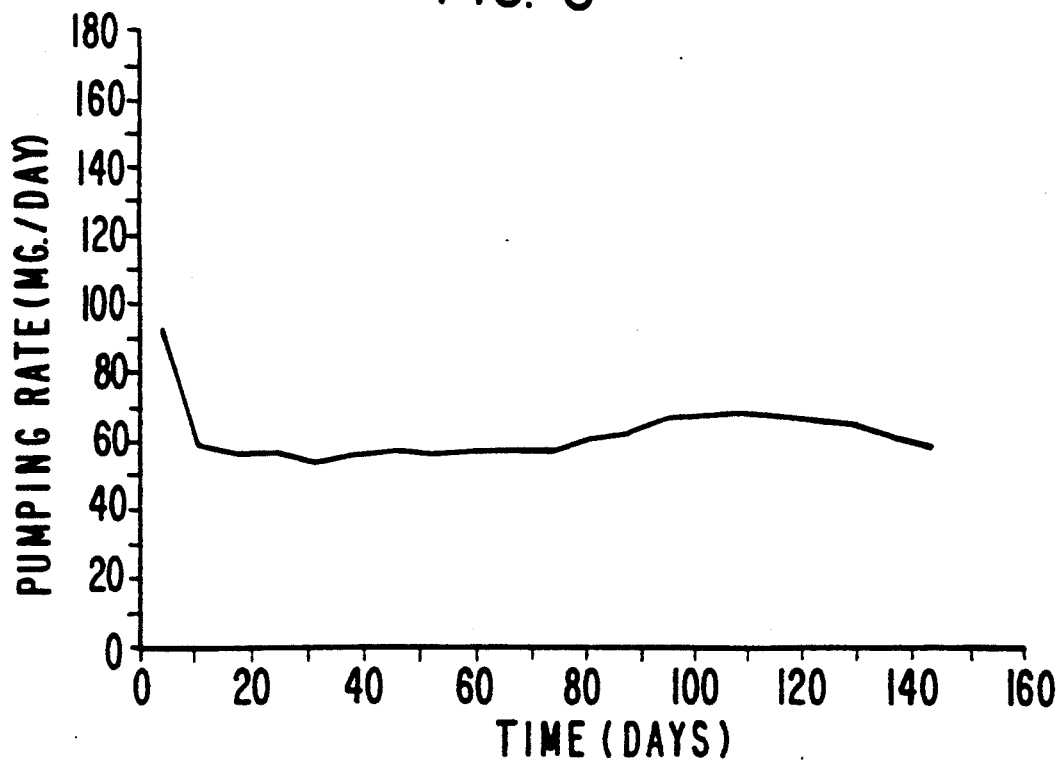
FIG. 6 is a graph that depicts the release rate pattern of a prehydrated delivery device according to the present invention.

FIG. 6 depicts the in vivo release rate for a delivery device made according to this procedure, showing the improved, immediate startup of delivery of ivermectin to the animal, in contrast to the delayed delivery of the non-prehydrated device of Example 1 (FIG. 5).

EXAMPLE 3

A prehydrated delivery device for the controlled delivery of the beneficial drug ivermectin with instant start-up was made as set forth in Example 1, except as follows: The delivery device of Example 1 was placed in an impermeable package together with 2-3 mL of distilled water. The package was sealed and stored at room temperature for at least one month and up to three months prior to use.

EXAMPLE 4

A delivery device for the controlled delivery of ivermectin without early start-up was made as set forth in Example 1, except as follows: During assembly, after the osmotic expansion tablet was placed in the membrane cup, a rigid porous dry reservoir was placed on top of the tablet inside the membrane cup. The reservoir was in the shape of a disk 0.26 inches thick and of a diameter such that the edge of the disk was in contact with the membrane wall. The reservoir was made of porous ultra-high molecular weight polyethylene (Porex ®). To compensate for the reservoir volume, only 1.5 g of the partition layer formulation and 8.5 g of the ivermectin formulation were incorporated into the device.

Figure 7:
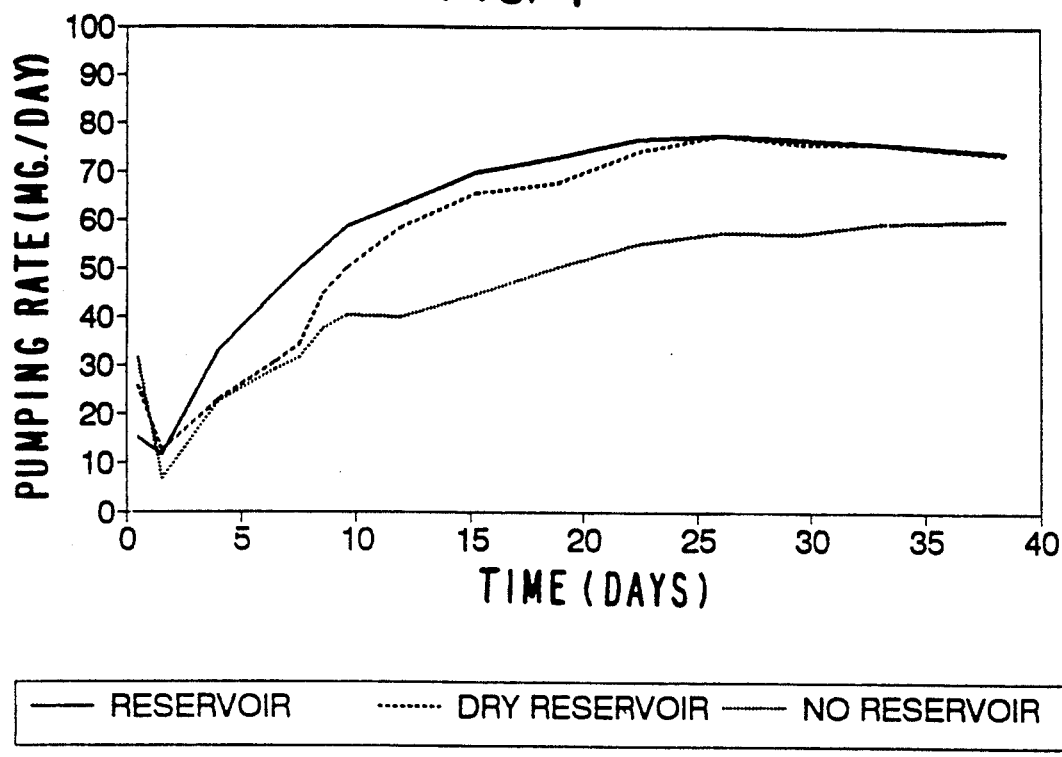
FIG. 7 is a graph that depicts the release rate patterns of a prehydrated delivery device according to the present invention and of two non-prehydrated delivery devices.

FIG. 7 depicts the in vitro release rate for a device made according to this procedure.

EXAMPLE 5

A delivery device for the controlled delivery of ivermectin with early start-up was made as set forth in Example 4, except that after the rigid porous dry reservoir was placed on top of the osmotic tablet inside the membrane cup, 1.0 g of water was placed on the reservoir and allowed to soak in.

FIG. 7 depicts the in vitro release rate for a device made according to this procedure, showing the improved start-up of delivery of ivermectin over that of the device of Example 4, with the dry reservoir, and that of Example 1, without a reservoir or prehydration.

EXAMPLE 6

A delivery device for the controlled delivery of ivermectin without early start-up was made as set forth in Example 1, except as follows: After the osmotic expansion tablet was placed in the membrane cup, a rigid porous dry reservoir was placed on top of the tablet inside the membrane cup. The reservoir was in the shape of a disk 0.33 inches thick and 0.53 inches in diameter such that a 0.1 inch gap existed between the reservoir and the membrane wall. The reservoir was made of porous ultra-high molecular weight polyethylene (Porex ®). Next, 2.5 g of melted partition layer formulation was added, forming a layer which separated the reservoir from the membrane wall and from the ivermectin formulation (7.1 g).

Figure 8:
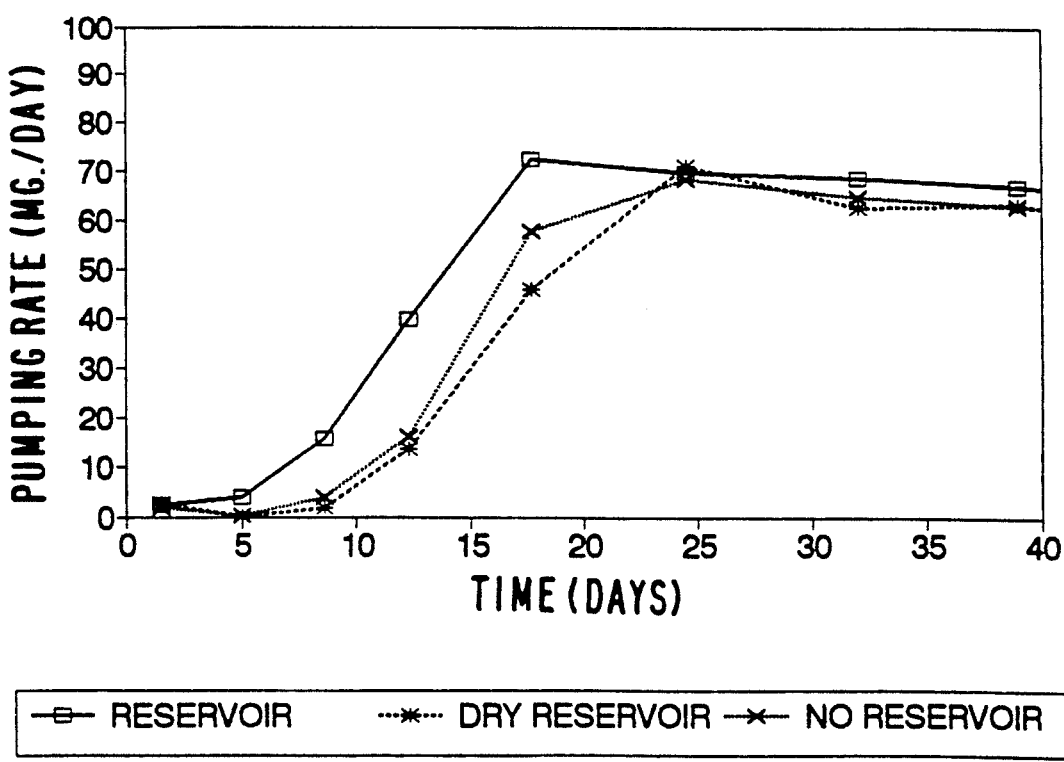
FIG. 8 is a graph that depicts the release rate patterns of a prehydrated delivery device according to the present invention and of two non-prehydrated delivery devices.

FIG. 8 depicts the in vitro release rate for a device made according to this procedure.

EXAMPLE 7

A delivery device for the controlled delivery of ivermectin with early start-up was made as set forth in Example 6, except that after the rigid porous dry reservoir was placed on top of the osmotic tablet inside the membrane cup, 1.2 g of water was placed on the reservoir and allowed to soak in before addition of the partition layer formulation.

FIG. 8 depicts the in vitro release rate for a device made according to this procedure, showing the improved start-up of delivery of ivermectin over that of the device of Example 6, with a dry reservoir, and that of Example 1, without a reservoir or prehydration.

Inasmuch as the foregoing specification comprises preferred embodiments of the invention, it is understood that variations and modifications may be made herein in accordance with the inventive principles disclosed, without departing from the scope of the invention.

What is claimed is:

1. An improved delivery device for delivering a beneficial agent to an environment of use over a prolonged period of time of 23 days or longer, the delivery device comprising:
   i) a wall that surrounds an internal compartment;
   ii) a beneficial agent formulation in the compartment;
   iii) an expandable fluid-activated driving member in the compartment, and
   iv) exit means in the wall; wherein the improvement comprises a prehydration permeant in the delivery device in contact with the expandable driving member, the prehydration permeant being in an amount of from about 0.025 g to 10 g, the amount being greater than 1% of the weight of the expandable driving member, the prehydration permeant being selected from the group consisting of water, distilled water, purified water, a biologically acceptable fluid and a buffer.

2. An improved delivery device according to claim 1, wherein the prehydration permeant is added during manufacture of the delivery device.

3. An improved delivery device according to claim 1, wherein the delivery device comprises from 0.1 g to 3 g of the prehydration permeant.

4. An improved delivery device according to claim 1, wherein the amount of prehydration permeant is about 5% to 40% by weight of the expandable driving member.

5. An improved delivery device according to claim 1, wherein the prehydration permeant is activated between room temperature and 50° C.

6. An improved delivery device according to claim 1 which further comprises a density element.

7. An improved delivery device according to claim 1, wherein the environment of use is a human.

8. An improved delivery device according to claim 1, wherein the environment of use is an animal.

9. An improved delivery device according to claim 6, wherein the environment of use is a ruminant animal.

10. An improved delivery device according to claim 1 which further comprises a partition layer between the beneficial agent formulation and the expandable driving member.

11. An improved delivery device according to claim 1, wherein the beneficial agent formulation comprises a drug in a thermo-responsive composition.

12. An improved delivery device according to claim 1, wherein the expandable driving member is selected from an osmopolymer, an osmagent, or a mixture of an osmagent in an osmopolymer.

13. An improved delivery device according to claim 11, wherein the drug is ivermectin; the expandable driving member is selected from an osmopolymer, an osmagent, or a mixture of an osmagent in an osmopolymer; and the delivery device further comprises a partition layer between the beneficial agent formulation and the expandable driving member and also further comprises a density element.

14. An improved delivery device according to claim 1 which exhibits substantially immediate delivery of the beneficial agent to the environment of use.

15. An improved delivery device for delivering a beneficial agent to an environment of use over a prolonged period of time of 23 days or longer, the delivery device comprising:

i) a wall that surrounds an internal compartment,
 ii) a beneficial agent formulation in the compartment,
 iii) an expandable fluid-activated driving member in the compartment, and
 iv) exit means in the wall;

wherein the improvement comprises a permeant reservoir containing a prehydration permeant in the compartment, the prehydration being in an amount of from about 0.25 g to 10 g, the amount being greater than 1% of the weight of the expandable driving member, the prehydration permeant being selected from the group consisting of water, distilled water, purified water, a biologically acceptable fluid and a buffer.

16. An improved delivery device according to claim 15 wherein the permeant reservoir is comprised of a porous material.

17. An improved delivery device according to claim 15 wherein the device further comprises a partition layer between the beneficial agent formulation and the expandable driving member.

18. An improved delivery device according to claim 15 which further comprises a density element.

19. An improved delivery device according to claim 15 wherein the permeant reservoir is in contacting relation with the expandable driving member.

20. A process for shortening the time to startup of release of a beneficial agent from a long-term delivery device into an environment of use, the delivery device comprising:

i) a wall that surrounds an internal compartment,
 ii) a beneficial agent formulation in the compartment,
 iii) an expandable fluid-activated driving member in the compartment, and
 iv) exit means in the wall;

wherein the process comprises the step of prehydrating the device with a prehydration permeant, where the amount of prehydration permeant is from about 0.025 g to 10 g, the amount being greater than 1% of the weight of the expandable driving member, for providing early beneficial agent release from the device, the prehydration permeant being selected from the group consisting of water, distilled water, purified water, a biologically acceptable fluid and a buffer.

21. A process according to claim 20 wherein the process comprises prehydrating the delivery device with up to 3 g of the prehydration permeant that enters the device.

22. A process according to claim 20 wherein the delivery device is prehydrated by spraying the device with the prehydration permeant, by dipping the device in the prehydration permeant, or by immersing the device in the prehydration permeant.

23. A process according to claim 20 wherein the delivery device is prehydrated by placing the device and the prehydration permeant together in an impermeable package.

24. A process according to claim 20 wherein the delivery device is prehydrated by placing the prehydration permeant into the device and in contact with the expandable driving member at the time of manufacture of the device.

25. A process according to claim 20 the delivery device is prehydrated by placing a permeant reservoir containing the prehydration permeant into the device at the time of manufacture of the device.

26. A process according to claim 20 wherein the prehydration permeant is selected from water, distilled water, purified water, a biologically acceptable fluid, and a buffer.

27. A process according to claim 20 wherein the expandable driving member is selected from an osmopolymer, an osmagent or a mixture of an osmagent in an osmopolymer, and the process comprises internally prehydrating the delivery device with from 0.1 g to 3 g of the prehydration permeant.

28. A process according to claim 20 wherein the expandable driving member is selected from an osmopolymer, an osmagent or a mixture of an osmagent in an osmopolymer, and the process comprises prehydrating the delivery device with the prehydration permeant in an amount of up to 40% of the weight of the expandable driving member.

29. A process according to claim 20 wherein prehydrating the device provides substantially immediate beneficial agent release from the device after the device is placed in the environment of use.

30. A process according to claim 20 wherein the device further comprises a density element.

31. A process according to claim 20 wherein the device further comprises a partition layer between the beneficial agent formulation and the expandable driving member.

* * * * *